(12) United States Patent
Hsu et al.

(10) Patent No.: US 9,845,459 B2
(45) Date of Patent: Dec. 19, 2017

(54) METHOD OF OBTAINING HIGH PURITY STEM CELLS FROM TISSUE

(71) Applicant: National Taiwan University, Taipei (TW)

(72) Inventors: Shan-Hui Hsu, Taipei (TW); Guo-Shiang Huang, Taipei (TW); Niann-Tzyy Dai, Taipei (TW); Lien-Guo Dai, Taipei (TW)

(73) Assignee: National Taiwan University, Taipei (TW)

(*) Notice: Subject to any disclaimer, the term of this patent is extended or adjusted under 35 U.S.C. 154(b) by 72 days.

(21) Appl. No.: 14/493,997

(22) Filed: Sep. 23, 2014

(65) Prior Publication Data
US 2015/0087063 A1 Mar. 26, 2015

(30) Foreign Application Priority Data
Sep. 25, 2013 (TW) .............................. 102134504 A

(51) Int. Cl.
*C12N 5/0775* (2010.01)

(52) U.S. Cl.
CPC ........ *C12N 5/0667* (2013.01); *C12N 2533/72* (2013.01)

(58) Field of Classification Search
None
See application file for complete search history.

(56) References Cited

U.S. PATENT DOCUMENTS 5,993,661 A * 11/1999 Ruckenstein ...... B01D 39/1676
                                                         210/231
2014/0315303 A1* 10/2014 Huang .................... G01N 1/31
                                                         435/366

FOREIGN PATENT DOCUMENTS

WO    WO2013069503    * 5/2013    ............. C12N 5/071

OTHER PUBLICATIONS

Cheng et al., The influence of spheroid formation of human adipose-derived stem cells on chitosan films on stemness and differentiation capabilities, Biomaterials, vol. 33, 2012, pp. 1748-1758.*
English translation of WO2013/069503, retrieved from Google Translate, Nov. 6, 2015, pp. 1-6.*
Boeuf et al., Chondrogenesis of mesenchymal stem cells: role of tissue source and inducing factors, Stem Cell Research & Therapy, vol. 1, 2010, pp. 1-9.*
Cell Strainer (BD Labware), 70 μm Cell Strainer, retrieved from the internet Nov. 6, 2015: www.amazon.com/Cell-Strainer-Falcon-%C2%B5m-case/dp/B0017UC1XQ.*

* cited by examiner

*Primary Examiner* — Thane Underdahl
*Assistant Examiner* — Evelyn Y Pyla
(74) *Attorney, Agent, or Firm* — WPAT, P.C., Intellectual Property Attorneys; Anthony King

(57) ABSTRACT

The present invention relates to a method of obtaining high purity stem cells from tissue, comprising: providing an impurity-containing cell mass obtained from a tissue; providing a filter device which comprises a cylinder structure, wherein the cylinder structure comprise an inlet and an outlet below and a content configured inside the cylinder structure between the inlet and the outlet; culturing the impurity-free cell mass on a polymeric film, wherein target stem cells of the impurity-free cell mass conjugate into a spheroid cell population; collecting the spheroid cell population from the polymeric film to obtain high purity target stem cells. According to the method of the present invention, stem cells can be rapidly and easily obtained from tissue. Only a small amount of tissue sample is required and the stem cells obtained can be readily used in clinical applications such as autotransplantation without the requirement of in vitro amplification.

6 Claims, 9 Drawing Sheets

METHOD OF OBTAINING HIGH PURITY STEM CELLS FROM TISSUE

CROSS-REFERENCES TO RELATED APPLICATIONS

This application claims priority to Taiwan Patent Application No. 102134504 filed on 25 Sep. 2013. All disclosure of which is incorporated herein by reference in its entirety.

BACKGROUND OF THE INVENTION

1. Field of the Invention

The present invention is related to a method of obtaining high purity stem cells from tissue. Particularly, the method of the present invention comprises using a filter device comprising a content to separate impurities from an impurity-containing cell mass and culturing target stem cells on a polymeric film.

2. The Prior Arts

Stem cells are undifferentiated cells capable of self-renewing and multilineage differentiation, which play important roles in a living organism in regard to the development from embryo to mature individual. Even when matured, stem cells still present throughout the living organism and are responsible for the renewing and regeneration of cells among tissues and organs. Stem cells are considered applicable for the treatment of several illnesses such as cancer, Parkinson's disease, Alzheimer's disease, cardiovascular diseases, and immune deficiency syndromes. In recent years, owing to many researches and breakthroughs in the field of stem cell study and biomedical material, stem cells have become one of the important sources of regenerative medicine for the treatment, repair, and rebuilt of damaged human organ tissues.

In terms of functionality, stem cells are multipotent. That is to say, stem cells are able to differentiate into different tissues and organs. Stem cells can be divided into embryonic stem cells and adult stem cells according to their origins. Embryonic stem cells are from the inner cell mass of early embryo sac and remain at the undifferentiated state. Embryonic stem cells are pluripotent stem cells that can differentiate into all cells from the three germ layers of the embryo. Yet, apart from the perfect abilities of renewing and differentiation, the use and obtaining of embryonic stem cells are still of great moral criticism. Adult stem cells, on the other hand, are undifferentiated cells found in mature tissues and are proven obtainable from tissues and organs such as bone marrow, skin, brain, skeletal muscles, and liver. Adult stem cells can self-replicate and differentiate into cells with the functionality of the tissue or organ from which they are originated. The purpose of adult stem cells is to replenish the lost cells under normal metabolism. For adult stem cells, in addition to differentiating into cells with the functionality of the tissue or organ from which they are originated, they can also differentiate into cells with the functionality of other tissues. The use of adult stem cells nowadays lies particularly in the filed of clinical applications since the survival rate of adult stem cells is high and the immunologic rejection is low after transplantation.

The common methods to isolate adult stem cells from tissues utilize density centrifugation to remove tissue fluid and enzymatic digestion followed by extraction to obtain primary cells. Such primary cells are then cultured and selected to give adhesive stem cells. The conventional methods as described above are easily contaminated and require complicate steps of centrifugation and isolation. Although integrated system of sterilized mixer and centrifuge or sealed tubular isolation device for the purpose of decreasing the chance of contamination are available, the purity and yield of stem cells using such system or device are low. In other words, there are still several drawbacks concerning the conventional method of obtaining adult stem cells from tissues such as low purity of the stem cells isolated, risk of contamination and mutation, which are result from contacting with impurities and other heterocytes such as endothelial cells and fibroblasts during the isolation process. These drawbacks largely affect the ability of renewing and differentiation of the stem cells obtained.

Conventionally, immunologic selections are used in order to solve the problem caused by heterocytes, in which flow cytometry or magnetic beads conjugated with antibodies specific to some surface antigens are used to perform stem cell selection. However, the surface antigens of the adult stem cells lack specificity and unity. Furthermore, the adult stem cells from different tissues or different species exhibit different levels of expression of surface antigens. Thus, the selection of adult stem cells via surface antigens cannot effectively cure the defect of the purity of isolated stem cells. Besides, amplifying a large number of cells is required prior to selection using antibodies in order to overcome the lost of cell viability and number caused by the interaction between cells and antibodies during the selection process, which, further increase the duration and cost of the whole isolation and selection process.

For the convenience and applicability of clinical application, a method of obtaining high purity stem cells from tissues is desired and such method should also be able to prevent in vitro contamination of heterocytes or other impurities in the environment that reduces the stemness of the stem cells obtained. Hence, a rapid, simple, and effective method of obtaining high purity stem cells from tissue is of urgent necessity.

SUMMARY OF THE INVENTION

As a result, the present invention provides a method of obtaining high purity stem cells from tissue, comprising: (a) providing an impurity-containing cell mass from a tissue; (b) providing a filter device including: a cylinder structure having an inlet and an outlet, the outlet is configured below the inlet, and the impurity-containing cell mass flows into the filter device via the inlet; and a content, configured inside the cylinder structure between the inlet and the outlet for separating the impurities from the impurity-containing cell mass and allowing an impurity-free cell mass to pass through the outlet; (c) recovering the impurity-free cell mass; (d) culturing the impurity-free cell mass on a polymeric film, wherein target stem cells of the impurity-free cell mass conjugate into a spheroid cell population; and (e) collecting the spheroid cell population from the polymeric film to obtain high purity target stem cells; wherein the content is selected from the group consisting of matrix, membrane, mesh, and any combination thereof, and a number of the high purity target stem cells increased at least 3-fold after incubation for 7 days. The diameter of pores of the content is 50 μm to 300 μm, and preferably, 50 μm to 150 μm. The tissue can be bone marrow, umbilical cord blood, peripheral blood, subcutaneous adipose tissue, or dental tissue, and wherein when the tissue is subcutaneous adipose tissue, the content separates at least 50% oil drops of the impurity-containing cell mass. The amount of the impurity-containing cell mass is at least 1 mL, for example, 1 mL to 5 mL, and the matrix is made of at least one material selected from the group consisting of chitosan, sulfonated chitosan, and chitosan-heparin.

In one embodiment of the present invention, the formation of the matrix comprises dissolving chitosan in an acidic solution to form a mixture, and the acidic solution is selected from the group consisting of acetic acid, formic acid, nitric acid, hydrochloric acid, percholoric acid, and sulfuric acid. The formation of the matrix further comprises injecting the mixture into the cylinder structure and allowing the mixture to solidify therein.

In one embodiment of the present invention, the polymer of the polymeric film is chitosan, sulfonated chitosan, alginic acid salt, polycaprolactone, or any combination thereof.

In one embodiment of the present invention, the filter device separates the impurities from the impurity-containing cell mass. The impurity-free cell mass after filtration is collected, which comprises stem cells, fibroblasts, erythrocytes, leukocytes, platelets, endothelial cells, pericyte, or smooth muscle cells.

In one embodiment of the present invention, the high purity target stem cells are CD271-positive stem, and the expression of CD271 thereof is at least 3-fold higher than a stem cell obtained using tissue culture polystyrene (TCPS).

The method of obtaining high purity stem cells from tissue according to the present invention, which utilizes the content for separating impurities, does not require expensive equipments or complicated procedure. Moreover, by culturing the impurity-free cell mass on the polymeric film, target stem cells can conjugate into a spheroid cell population, whereas the sub-colonies of heterocytes can only adhere to the polymeric film and grow thereon. Hence, the method of the present invention can effectively select high purity target stem cells with good stemness and differentiation ability. Meanwhile, the method of obtaining high purity stem cells from tissue according to the present invention is not limited by the amount of sample or primary cell used, that is to say, a small amount of tissue is sufficient for separation and selection of stem cells, which can then be directly used in clinical applications.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

BRIEF DESCRIPTION OF THE DRAWINGS

FIG. 6B indicates the ability of adipogenic differentiation of the subcutaneous adipose stem cells; and FIG. 6C indicates the ability of chondrogenesis differentiation of the subcutaneous adipose stem cells.

DETAILED DESCRIPTION OF THE PREFERRED EMBODIMENT

Definition

Figure 1:
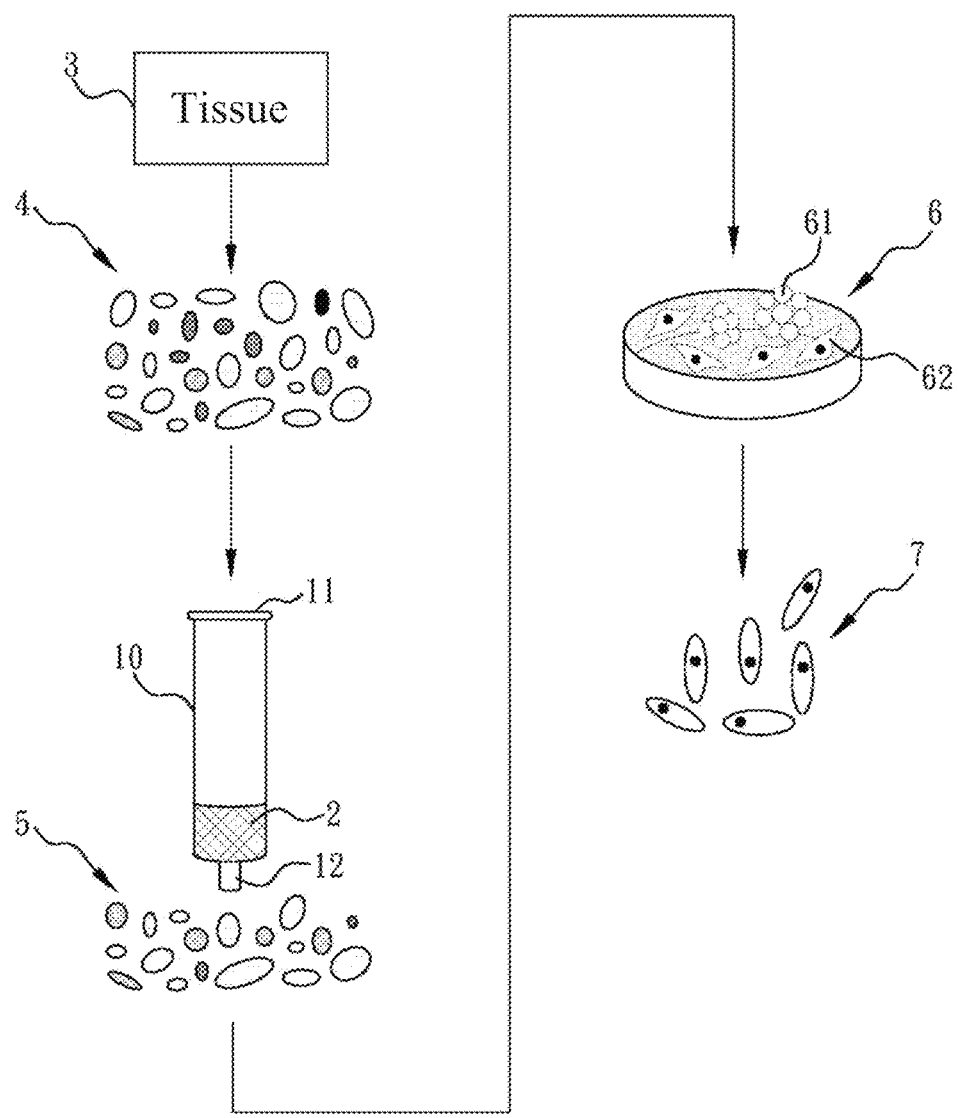
FIG. 1, the flow chart of using the matrix to filter and the polymeric film to collect target stem cell.

As used herein, the term "filter device" refers to an object that is able to filter and/or adsorb impurities. For the process of filtration, when the impurity-containing cell mass pass through matrix and/or mesh, the impurities are separated and removed. For the process of adsorption, when the impurity-containing cell mass are made contact with membrane, the impurities are adsorbed onto the membrane.

As used herein, the term "membrane" comprises polymeric film and/or adsorptive membrane.

In order to confirm that the method of obtaining high purity stem cells from tissue according to the present invention is rapid, simple, and effective, the present invention firstly provides an impurity-containing cell mass from a tissue. Then, a filter device having matrix which is able to simultaneously separate the impurities from the impurity-containing cell mass and collect an impurity-free cell mass is also provided. In addition, the present invention provides a polymeric film to collect target stem cells from the impurity-free cell mass in the form of conjugated spheroids. Finally, the morphology, stemness gene expression, growth rate, and ability of differentiation of the target stem cells obtained are evaluated.

Material

1. Preparation of the Matrix

The content of the present invention comprises matrix, membrane, mesh, and any combination thereof. In one embodiment of the present invention, the content is a matrix made by freeze-drying described as follow: Firstly, the matrix was dissolved in an acidic solution to make a polymeric solution. The acidic solution was selected from the group consisting of acetic acid, formic acid, nitric acid, hydrochloric acid, perchloric acid, and sulfuric acid, and, preferably, acetic acid or formic acid. The matrix was made of chitosan, sulfonated chitosan, or chitosan-heparin. In one embodiment of the present invention, chitosan of molecular weight of 510 kDa (Fluka, USA) was dissolved in 2 vol % acetic acid to make a chitosan solution. The chitosan solution prepared was subjected to deaeration. Then, the deaerated chitosan solution was poured into a cylinder structure such as a syringe and placed under −20° C. for solidification. The solidified chitosan solution was then immersed in 50/50 v/v 1 N NaOH/EtOH solution. After solvent exchange and matrix gelation under −20° C., the matrix was washed to eliminate the remaining NaOH and salt.

The chitosan matrix prepared according to the above method has pores of diameter of 50 µm to 300 µm, preferably, 50 µm to 150 µm.

2. Preparation of the Polymeric Film

The polymer of the polymeric film can be chitosan, sulfonated chitosan, alginic acid salt, polcaprolactone, or any combination thereof. In one embodiment of the present invention, chitosan was used as an exemplary material for the polymeric film. Firstly, chitosan of molecular weight of 510 kDa (Fluka, USA) having 77.7% degree of deacetylation was purchased. 0.5 g of such chitosan powder was dissolved in 49.5 mL double-distilled water. After stirring for 30 minutes at room temperature, 0.5 mL of acetic acid was added and was further stirred for 12 hours at room temperature and left overnight. Mesh of size of 100 μm was used to filter 1% chitosan solution to remove impurities. Then, 300 μL of 1% chitosan solution was evenly coated onto glass slide of thickness of 1.5 cm. When the glass side coated with the chitosan solution was dried, it was immersed in NaOH for 5 minutes. After the immersion, the glass slide was washed by a large amount of phosphate buffered saline (PBS) and then dried to give chitosan polymeric film.

The analytical results of the present invention are presented as means±standard deviation, and t-test is used to evaluate data of statistics. P-values smaller than 0.05 indicate statistical significances.

Please refer to FIG. 1, the flow chart of using the matrix to filter and the polymeric film to collect target stem cell according to the present invention. Firstly, an impurity-containing cell mass 4 was isolated from a tissue 3. A filter device 10 was used to separate impurities from the impurity-containing cell mass 4, in which the impurity-containing cell mass 4 was injected from an inlet 11 and passed through an outlet 12. The filter device 10 comprises a content 2. An impurity-free cell mass 5 can thus be collected. Then, the impurity-free cell mass 5 was cultured on a polymeric film 6. Heterocytes 62 such as fibroblasts, erythrocytes, leukocytes, platelets, endothelial cells, pericytes, or smooth muscle cells can only adhere to the polymeric film 6 and grow thereon, whereas the target stem cells of the impurity-free cell mass can conjugate into a spheroid cell population 61. Such spheroid cell population 61 can then be removed by patting and collected to yield high purity target stem cells 7.

The method of the present invention only requires a small amount of sample and can yield target stem cells in a short period of time. For 1 mL of bone marrow fluid and 1 mL of umbilical cord blood, stem cells can be yield within 3 hours; for 3 mL of peripheral blood, stem cells can also be yield within 3 hours; for 5 mL of subcutaneous adipose tissue, stem cells can be yield within 6 hours. For dental tissue, only 0.1 mL of sample is required to yield target stem cells. Such stem cells yield by the method of the present invention exhibit high ability of differentiation as well as fast growth rate, thus, are suitable for amplification and culture. Subcutaneous adipose tissues are used as exemplary source to give stem cells in the following examples.

EXAMPLE 1

Isolate the Impurity-Containing Cell Mass from Subcutaneous Adipose Tissue

Firstly, subcutaneous adipose tissues obtained via liposuction was washed by PBS several times and cut into pieces using surgical scissors. Equal volume of 200 U/mL Type I collagenase (Sigma)/Hank's balanced salt solution (HBSS) was added and was shook in incubator at 37° C. (See Table 2 for the composition of HBSS). Centrifugation was used to remove undigested fat chunks after the incubation. Then, a cell mesh of pore diameter of 70 μm was used to give primary cells. After loaded onto culture dishes, the primary cells were then dissolved using culture medium and transferred to 75T-flask (BD Bioscience) (See Table 1 for the composition of culture medium). After the cells growth reaching about eight-tenth of the volume of the flask, 0.5% Trypsin/2-[2-(Bis(carboxymethyl)amino)ethyl-(carboxymethyl)-amino]acetic acid (EDTA) (Gibco) was used to sub-culture the primary cells, which is referred as impurity-containing cell mass in the present invention.

TABLE 1

| Components | Concentration | Manufacturer |
|---|---|---|
| Dulbecco's modified eagle medium-low glucose (DMEM-LG) | | |
| DMEM (Low glucose) | 1000 g/L | Sigma |
| Sodium bicarbonate (NaHCO$_3$) | 3.7 g/L | Sigma |
| F12 | | |
| F12 nutrient mixture powder | 1000 g/L | Gibco |
| Sodium bicarbonate(NaHCO$_3$) | 1.173 g/L | Sigma |
| HEPES buffer solution(1M) | 10 ml/L | Gibco |
| BSA albumin fraction V solution, 7.5% | 13.5 ml/L | Gibco |
| Gentamicin reagent solution | 4 ml/L | Gibco |

TABLE 2

| Components | Concentration (g/L) |
|---|---|
| NaHCO$_3$ | 0.35 |
| KCl | 0.4 |
| KH$_2$PO$_4$ | 0.06 |
| NaCl | 8 |
| Na$_2$HPO$_4$•7H$_2$O | 0.09 |
| CaCl$_2$ | 0.14 |
| MgCl$_2$•6H$_2$O | 0.1 |
| MgSO$_4$•7H$_2$O | 0.098 |

EXAMPLE 2

Obtain Target Stem Cells on the Polymeric Film by Filtering the Impurity-Containing Cell Mass Using the Matrix-Filled Cylinder Structure The matrix was filled in the cylinder structure and was washed by PBS. The impurity-containing cell mass obtained from Example 1 was injected via an inlet on the matrix-filled cylinder structure. When the impurity-containing cell mass of Example 1 was derived from subcutaneous adipose tissue, the impurities are mostly oil drops. The flow speed was set at 0.5-2 mL/min, preferably, 1 mL/min, allowing the impurity-containing cell mass to pass through the matrix-filled cylinder structure for filtration. The filtration process lasted approximately 5 minutes.

Fluid flow through the matrix-filled cylinder structure, the impurity-free cell mass, was then collected at an outlet of the matrix-filled cylinder structure. When the impurity-containing cell mass of Example 1 was derived from subcutaneous adipose tissue, the content separates at least 50% oil drops of the impurity-containing cell mas. Then the impurity-free cell mass was then cultured on the polymeric film at the density of 1×10–1×10$^4$ cell/cm$^2$. After 12-14 hours culture, the polymeric film was placed under room temperature and the spheroids of conjugated cells were removed by patting and collected to yield target stem cells.

Figure 2A:
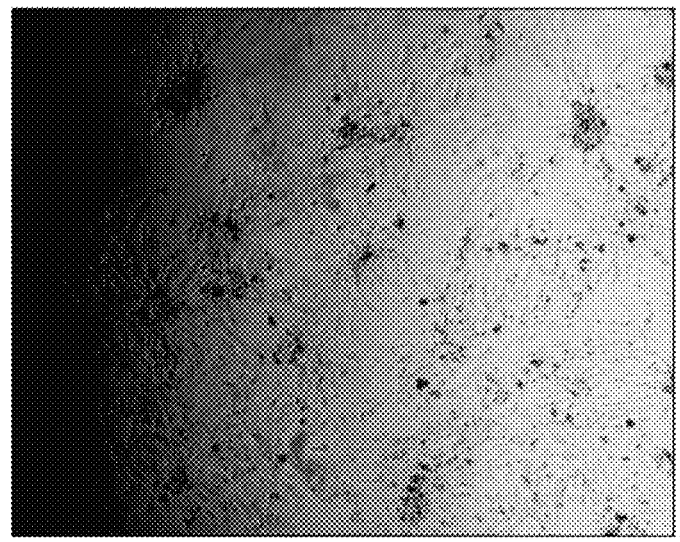
FIG. 2A, morphology of the cells on the polymeric film without removing the impurities by using the filter device. (Scale: 100 µm)
Figure 2B:
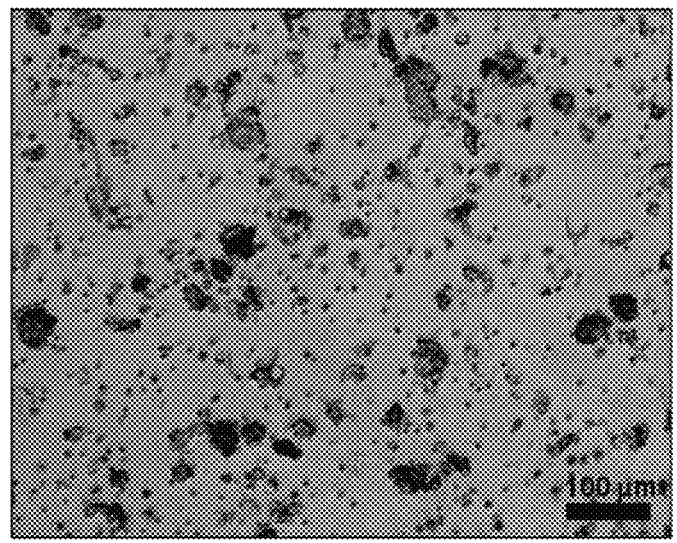
FIG. 2B, morphology of the cells on the polymeric film with removing the impurities by using the filter device. (Scale: 100 µm)

Please refer to FIG. 2A, the morphology of the cells on the polymeric film without removing the impurities by using the matrix-filled cylinder structure. Only a small proportion of cells gathered but not conjugated into spheroid cell populations on the polymeric film, and most of the cells thereon spread and adhered, which can not be used to select target stem cells. On the other hand, please refer to FIG. 2B, the morphology of the cells on the polymeric film with removing the impurities by using the matrix-filled cylinder structure, significant conjugation of cells into spheroid cell populations, approximately 60%, can be observed; hence, was suitable for further selection of the target stem cells.

Figure 3:
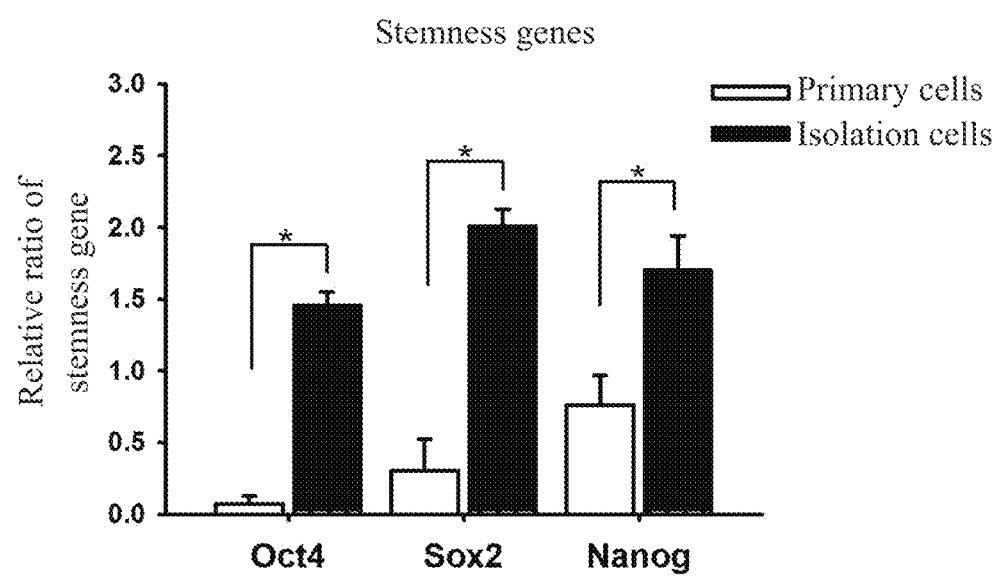
FIG. 3, mRNA expression of the stemness gene (Oct4, Sox2, and Nanog) of subcutaneous adipose stem cells.

Please refer to FIG. 3, the mRNA expression of the stemness gene (Oct4, Sox2, and Nanog) of subcutaneous adipose stem cells. Such mRNA expression is evaluated via Real-time polymerase chain reaction (RT-PCR) and indicates that the subcutaneous adipose stem cells exhibit significant superior stemnesses in regard to these 3 stemness genes comparing to those of the primary cells.

EXAMPLE 3

Growth Rate Analysis

Cells of the $1^{st}$ to $15^{th}$ sub-culture generations were used for the growth rate analysis. All cells were checked for the morphology by an inverted phase contrast microscope and for the proliferation (growth curve) by the DNA Hoechst 33528 dye stain assay and a fluorescence spectrophotometer with excitation at 365 nm and emission at 458 nm (Hitachi F2500). The cell doubling time was calculated from the growth curve.

Figure 4:
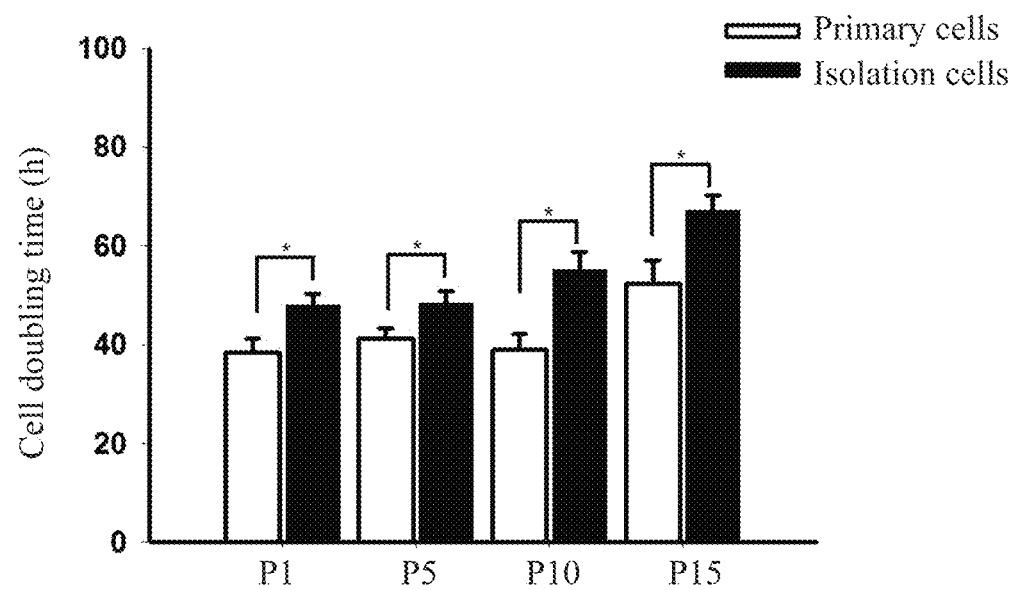
FIG. 4, comparison of the cell doubling time, wherein P indicates the subculture generation.

Please refer to FIG. 4, the comparison of the cell doubling time, in which the subcutaneous adipose stem cells obtained via the separation of the matrix according to the method of the present invention can be long-term sub-cultured up to 10 generations or above while maintaining a steady growth rate. Since stem cells of low purity, for instance, the stem cells mixed with other cells obtained from conventional methods known to the art, show decrease in growth rate when sub-cultured, they can not be sub-cultured into too many generations. The subcutaneous adipose stem cells obtained from conventional methods known to the art, for example, can only be sub-cultured for no more than 8-10 generations. Such limitation greatly affects further applications.

Figure 5:
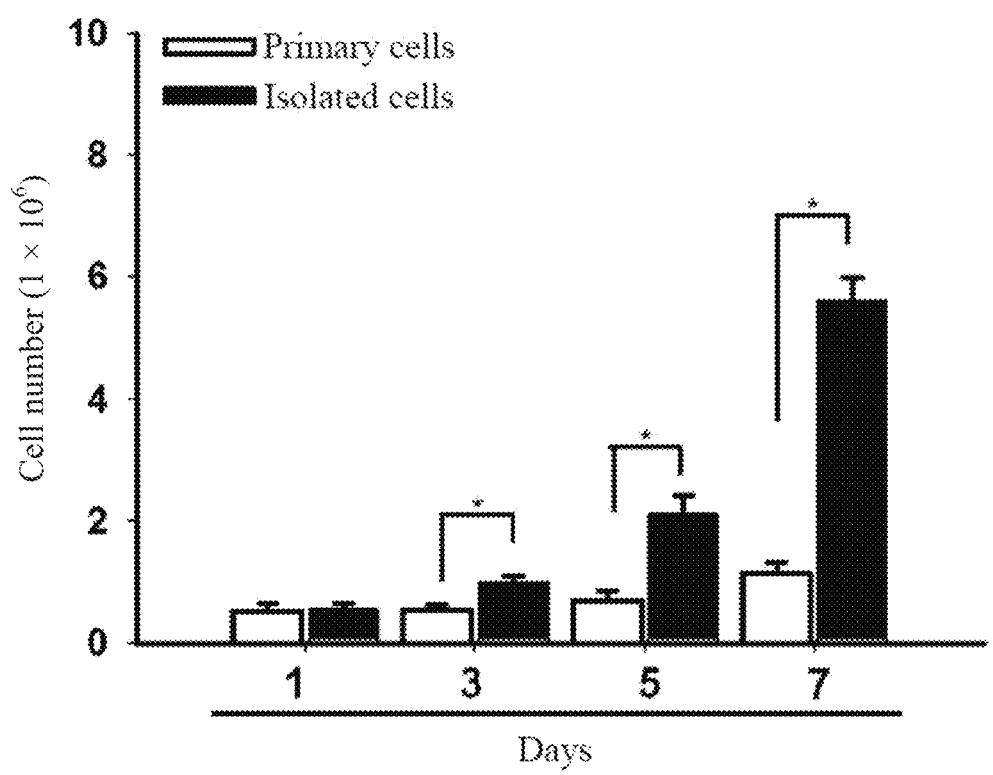
FIG. 5, comparison of the cell numbers over culturing time.

Please refer to FIG. 5, the comparison of the cell numbers over culturing time, in which the number of the subcutaneous adipose stem cells obtained via the separation of the matrix according to the method of the present invention usually increases by 3-fold after 7 days of culture. The increase in cell number varies according to the culture environment. As shown in FIG. 5, in the best scenario, the cell number of the subcutaneous adipose stem cells obtained via the separation of the matrix according to the method of the present invention can increase by 10-fold.

In one embodiment of the present invention, when the content was the combination of matrix and polymeric film, wherein the matrix was made of chitosan, sulfonated chitosan, or chitosan-heparin, and the polymeric film was made of chitosan, sulfonated chitosan, alginic acid salt, or polycaprolactone, the number of the subcutaneous adipose stem cells obtained thereof increases by 4-fold after 7 days of culture (Result not shown).

In another embodiment of the present invention, when the content was the combination of matrix and membrane, wherein the membrane is purchased from BD Falcon, the number of the subcutaneous adipose stem cells obtained thereof increases by 3.5-fold after 7 days of culture (Result not shown).

EXAMPLE 4

Abilities of Differentiation of the Subcutaneous Adipose Stem Cells
1. Osteogenic Differentiation For osteogenic differentiation, cells in a density of $3 \times 10^4$ cells/cm$^2$ were plated on tissue culture polystyrene (TCPS) in α-minimum essential medium (α-MEM) supplemented with 10% FBS, 10 µM β-glycerophosphate (Sigma), 0.2 µM ascobate-2-phosphate (Sigma), and $10^{-8}$ M dexamethasone (Sigma). The culture was maintained for three weeks. The medium was refreshed twice a week. The expression of runt-related transcription factor (Runx2) and osteocalcin (OCN) genes was analyzed by RT-PCR.

Figure 6A:
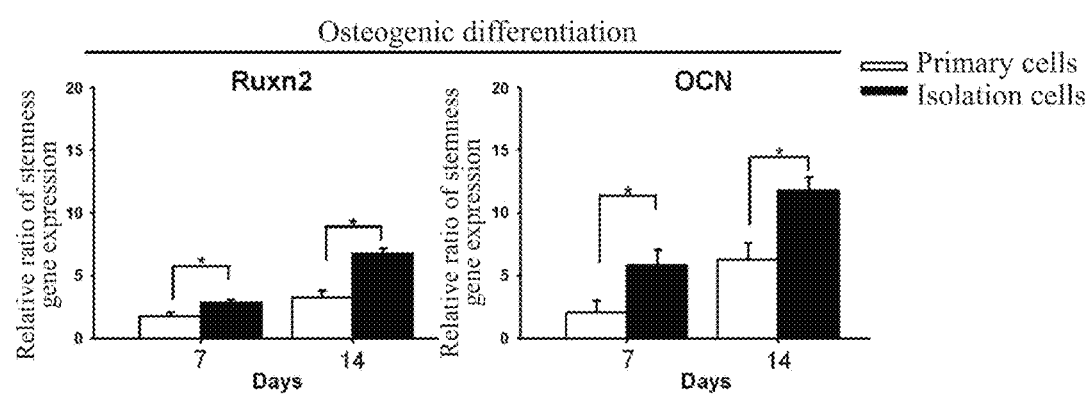
FIG. 6A-C, the ability of differentiation of the subcutaneous adipose stem cells, wherein FIG. 6A indicates the ability of osteogenic differentiation of the subcutaneous adipose stem cells.

As shown in FIG. 6A, the ability of osteogenic differentiation of the subcutaneous adipose stem cells obtained via the method of the present invention, both the subcutaneous adipose stem cells after 7 and 14 days of culture exhibit better abilities of osteogenic differentiation (Runx2 and OCN) comparing to those of primary cells. In particular, after 14 days of culture, the subcutaneous adipose stem cells show approximately twice the ability of osteogenic differentiation of the primary cells.

2. Adipogenic Differentiation

For adipogenic differentiation, cells in a density of $3 \times 10^4$ cells/cm$^2$ were cultured in high glucose DMEM (Gibco) supplemented with 10% FBS, 0.5 µM isobutyl-methylxanthine (Sigma), 200 µM indomethacin (Sigma), $10^{-6}$ M dexamethasone and 10 µg/ml insulin and cultured for three weeks. The induction medium was refreshed twice a week. The expression of peroxisome proliferator-activated receptor γ2 (PPARγ2) and lipoprotein lipase (LPL) genes was analyzed by RT-PCR.

Figure 6B:
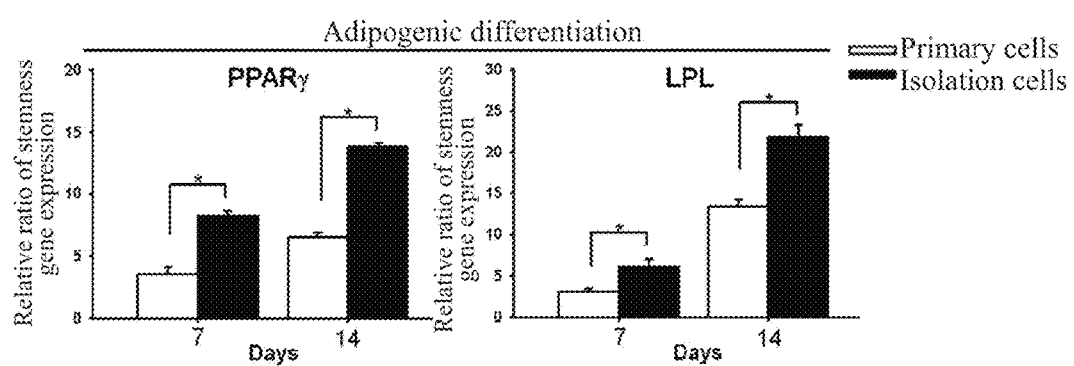

As shown in FIG. 6B, the ability of adipogenic differentiation of the subcutaneous adipose stem cells obtained via the method of the present invention, both the subcutaneous adipose stem cells after 7 or 14 days of culture exhibit better abilities of adipogenic differentiation comparing to the primary cells cultured after the same number of days accordingly. Moreover, the expressions of PPARγ2 are more significant than the expressions of LPL.

3. Chondrogenesis Differentiation

Pellet culture was used first to evaluate the chondrogenesis potential. Highly concentrated cells ($50 \times 10^4$ cells in 20 µL) were plated on polyester Transwells (0.4 µm pore size, Corning) in a 24-well tissue culture plate and incubated at 37° C. for 4 hours to allow cell encapsulation and overlaid with chondrogenesis induction medium for three weeks. The chondrogenesis induction medium was low glucose DMEM containing 10% FBS, 10 ng/ml TGF-β3 (Peprotech), 0.1 µM dexamethasone, 50 µg/mL L-ascobate-2-phosphate, 40 µg/mL L-proline (Sigma), 1% insulin transferrin selenium (ITS+premix) 100×(Sigma), and 1% penicillin-streptomycin and was changed twice a week. The chondrogenesis induction medium was added and cultured for another three weeks before the analysis of Sox9 and aggrecan (Aggr) gene expressions by RT-PCR.

Figure 6C:
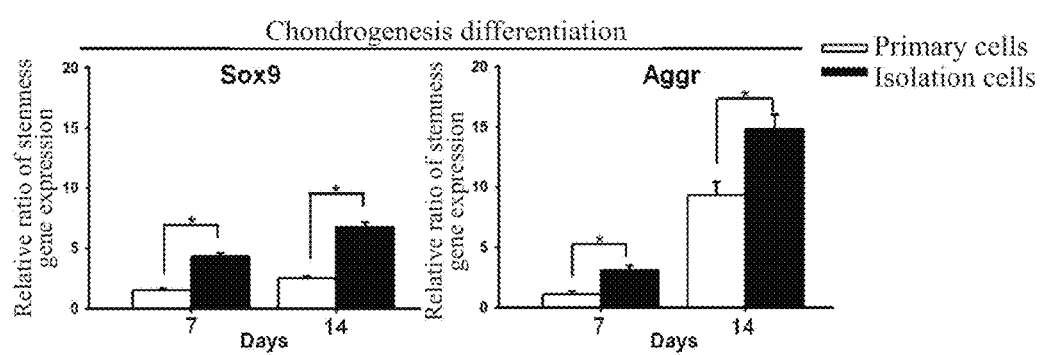

As shown in FIG. 6C, the ability of chondrogenesis differentiation of the subcutaneous adipose stem cells obtained via the method of the present invention, both the subcutaneous adipose stem cells after 7 or 14 days of culture exhibit better abilities of chondrogenesis differentiation comparing to the primary cells cultured after the same number of days accordingly. In addition, when the subcutaneous adipose stem cells are compared to the primary cells after culturing for the same number of days, the Sox9 and Aggr gene expressions of the subcutaneous adipose stem cells after 7 days are better than those cultured after 14 days.

Figure 7:
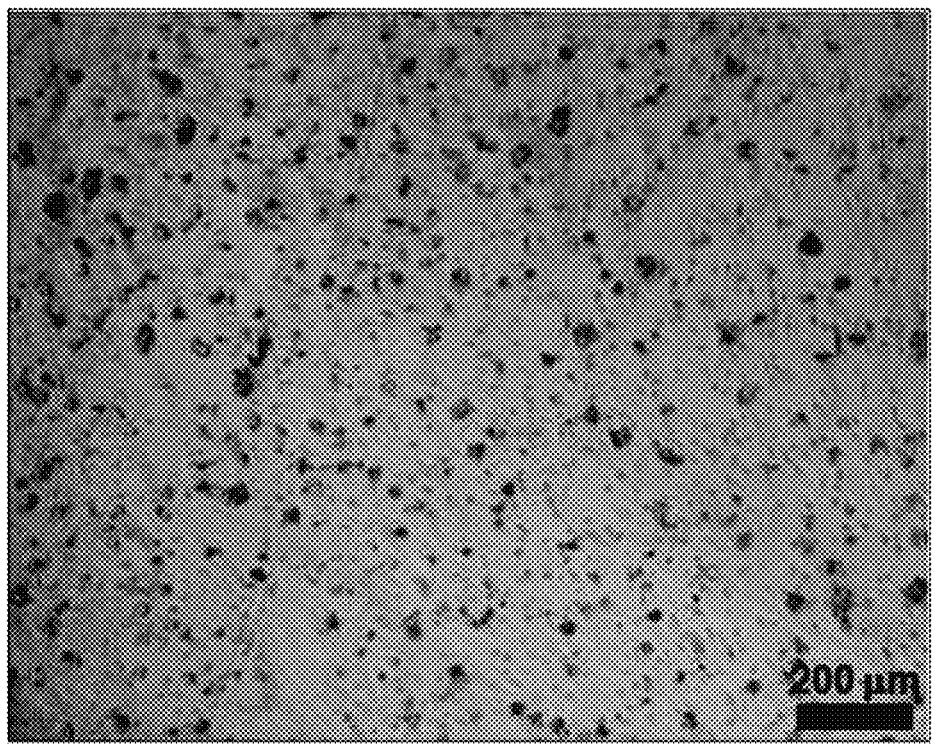
FIG. 7, morphology of the cells on the polymeric film with removing the impurities by using adsorptive membrane. (Scale: 200 µm)

In another embodiment of the present invention, the content was an adsorptive membrane, which is made of chitosan, sulfonate chitosan, alginic acid salt, polycaprolactone, or any combination thereof. Such adsorptive membrane was used to adsorb the impurity-containing cell mass, and the polymeric film was used to collect target stem cells. As shown in FIG. 7, the morphology of the cells on the polymeric film with removing the impurities by using adsorptive membrane, significant stem cells conjugated into spheroid cell populations, about 65%, can be observed. Hence, stem cells can be selected.

EXAMPLE 5

CD271 Positive Stem Cell Selection and Stemness Gene Expression

CD271, also known as the low-affinity nerve growth factor receptor (LNGFR) or p75 neurotrophin receptor (p75 NTR), is not a perivascular marker. CD271-positive bone marrow stem cells (BMSCs) are known to have greater expansion and a greater capacity to differentiate to adipocytes, osteoblasts, and chondrocytes, yet, the expression of CD271 was lost quickly after subculture. As shown in Table 3, all primary and sub-cultured generations (passage 0-3) of adipose-derived stem cells obtained via the method of the present invention (CS-ADSCs) have significant more CD271-positive stem cells than those obtained via conventional methods with tissue culture polystyrene (TCPS), indicating that the content and the polymeric film of the present invention interact with the heterocytes of stromal vascular fraction (SVF) to select CD271-positive stem cells by the formation of spheroid cell populations. All adipose stem cells obtained via conventional methods with TCPS show CD271 expression of lower than 20%; whereas, adipose stem cells obtained via the method of the present invention, particularly, in passage 2, show CD271 expression of up to 50%. In other word, the number of CD271-positive stem cells may increase in early passages as a result of the cell selection process during in vitro culture of the method of the present invention.

TABLE 3

| Adipose-derived stem cells (ADSC) | TCPS | CS-ADSCs |
| --- | --- | --- |
| Passage 0 | 4.9% | 15.4% |
| Passage 1 | 10% | 26-32% |
| Passage 2 | 13% | 40-50% |
| Passage 3 | 8% | 24-35% |

In addition, the adipose stem cells of passage 2 obtained via both the conventional method and the method of the present invention were subject to FoxD3 and Sox10 stemness gene analysis. It is observed that the relative ratio of stemness gene expression of the adipose stem cells obtained via the present invention increased about 2-fold or above when comparing to the relative ratio of stemness gene expression of the adipose stem cells obtained via conventional method (result not shown).

Conclusion

According to the above embodiments, the method of obtaining high purity stem cells from tissue of the present invention can separate impurities from the impurity-containing cell mass allowing stem cells in such impurity-containing cell mass to conjugate into spheroid cell populations and the further selection and collection of target stem cells therefrom. In particular, only a small amount of sample and a short period of time are required according to the method of the present invention, for example, stem cells can be isolated within 3 hours from 1 mL of bone marrow fluid, 1 mL of umbilical cord blood, and 3 mL of peripheral blood. Stem cells can also be isolated within 6 hours from 5 mL of subcutaneous adipose tissue. And for dental tissue, only 0.1 mL of sample is required to yield stem cells. Moreover, the stem cells obtained, as shown in the embodiments above, exhibit excellent stemness in regard to osteogenic, adipogenic, and chondrogenesis differentiation.

In summary, the method of obtaining high purity stem cells from tissue according to the present invention can rapidly and effectively isolate stem cells without the need of expensive equipments or complicated procedure. The isolated stem cells have good stemness and differentiation ability. Meanwhile, only a small amount of tissue is required to obtain stem cells according to the method of the present invention and the stem cells obtained can be readily used for clinical application, that is to say, samples from surgery can be directly utilized to isolate high purity and effective stem cells and be subjected to autotransplantation without in vitro amplification.

What is claimed is:

1. A method for chitosan matrix purification by absorbing oil drops to obtain high purity stem cells from tissue, consisting the steps of:
    (a) providing an oil drops-containing cell mass isolated from a tissue through a cell mesh of pore diameter of 70 μm;
    (b) providing a filter device including:
    a cylinder structure having an inlet and an outlet, the outlet is configured below the inlet, and the oil drops-containing cell mass flows into the filter device via the inlet; and
    a content, configured inside the cylinder structure between the inlet and the outlet for separating the oil drops from the oil drops-containing cell mass by absorbing oil drops and allowing an oil drops-free cell mass to pass through the outlet, and the diameter of pores of the content is 100 μm to 150 μm;
    (c) recovering the oil drops-free cell mass;
    (d) culturing the oil drops-free cell mass on a polymeric film wherein target stem cells of the oil drops-free cell mass conjugate into a spheroid cell population; and
    (e) collecting the spheroid cell population from the polymeric film to obtain high purity target stem cells;
    wherein the content in step (b) is formed by a matrix, the formation of the matrix comprises dissolving chitosan in an acidic solution to form a mixture, injecting the mixture into the cylinder structure and allowing the mixture to solidify therein; and the matrix is made of at least one material selected from the group consisting of chitosan, sulfonated chitosan, and chitosan-heparin, the matrix absorbs oil drops from the oil drops-containing cell mass to obtain oil drops-free cell mass, and the high purity stem cells have an at least 3-fold increase in number after incubation for 7 days without transferring to a tissue culture plate.

2. The method of claim 1, wherein an amount of the oil drops-containing cell mass is at least 1 mL.

3. The method of claim 1, wherein the acidic solution is selected from the group consisting of acetic acid, formic acid, nitric acid, hydrochloric acid, perchloric acid, and sulfuric acid.

4. The method of claim 1, wherein the oil drops-free cell mass comprises stem cells, fibroblasts, erythrocytes, leukocytes, platelets, endothelial cells, pericytes, or smooth muscle cells.

5. The method of claim 1, wherein the tissue is bone marrow, umbilical cord blood, peripheral blood, subcutaneous adipose tissue, or dental tissue.

6. The method of claim 1, wherein a polymer of the polymeric film is chitosan, sulfonated chitosan, alginic acid salt, polycaprolactone, or any combination thereof.

\* \* \* \* \*